United States Patent [19]

Mikkelsen

[11] Plant 5,132

[45] Nov. 1, 1983

[54] IMPATIENS PLANT

[75] Inventor: James C. Mikkelsen, Ashtabula, Ohio

[73] Assignee: Mikkelsens, Inc., Ashtabula, Ohio

[21] Appl. No.: 354,079

[22] Filed: Mar. 2, 1982

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

An impatiens plant known by the cultivar name Gemini, and characterized by its clear bright pink flower color and contrasting dark green variegated foliage; highly floriferous habit; firm petal texture; relatively large flowers, with distinct deep pink to red throat; continuous flowering and highly stable flower color, with little fading in summer, and by its semi-procumbent and weather resistant habits which make it ideal for baskets and bedding plants.

1 Drawing Figure

The present invention relates to a new and distinctive cultivar of Impatiens plant botanically known as Impatiens, and known by the cultivar name Gemini. The new cultivar was developed by me through controlled breeding in Ashtabula, Ohio. The seed parent was 79-1309-3 (Mikkelsen) and the pollen parent was 79-1164-1 (Mikkelsen). Asexual reproduction of terminal or stem cuttings has shown that the unique features of this new impatiens are stablized and are reproduced true to type in successive propagations.

The following characteristics distinguish Gemini from both its parent varieties and other cultivated impatiens of this type known and used in the floriculture industry:

1. A low, somewhat loosely growing plant that is set apart from other Mikkelsen hybrids by the distinctive clear bright pink flower color contrasting with dark green variegated foliage.

2. The new cultivar is highly floriferous, averaging 6–8 blooms per whorl; petal texture is firm, nearly approaching the texture of Columbia, disclosed in my pending application.

3. The individual flowers are further unique in possessing a distinct deep pink to red throat. Flower size is large, 6–7 cm. in diameter, with some flowers in specimen plants measuring up to 8 cm. in diameter.

4. The new cultivar is semi-procumbent and therefore ideal for baskets. Field trials demonstrate that Gemini is an excellent outdoor bedding plant, being highly resistant to weather damage; the cultivar looked as good in October as in August, the time the photographic drawing was taken.

5. Flowering is continuous outside until killing frost. Foliage shows very little "pinking" in the variegation in cool weather. Planting in full sunlight is essential for best qualities of this cultivar.

6. The dark red spur of the flowers is unusually long, measuring 7 cm.

7. Foliage tends to be long, narrow, concave and variegated with mid-vein red in yellow zone.

8. An unusual feature of this new cultivar is the stability of flower color winter and summer, with very little fading in full sunlight, with the reverse of petal being nearly the same color as top side.

The accompanying colored photograph taken in August in full sun illustrates the overall appearance of Gemini. The photo is essentially a top perspective view and shows the colors as true as it is reasonably possible to obtain in a colored reproduction of this type.

The following is a detailed description of my new impatiens cultivar based on plants produced under commercial practices in Ashtabula, Ohio. The illustrated specimen was planted outside in full sun the second week of June from a 4" pot. When the photo was taken in August, the single plant measured 50 cm. diameter by 25 cm. high. Color references are made to The Royal Horticultural Society Colour Chart except where general terms of ordinary dictionary significance are used.

Parentage: Mikkelsen seedling 79-1309-3 × Mikkelsen seedling 79-1164-1.

Propagation:

(A) *Stem cuttings.*—A cutting 15 mm. long will develop to 4 cm. in 21–24 days.

(B) *Time to initiate root.*—8–10 days at 23° C. summer.

*Time to initiate root.*—12–14 days at 20° C. winter.

(C) *Rooting habit.*—Very fibrous, dendritic, abundant.

Plant description:

(A) *Form.*—Low, symmetrical, self-branching, slightly procumbent flowering herb with red stems.

(B) *Habit of growth.*—Low, somewhat loosely growing, self-branching and semi-procumbent, with dark red stems; would not be classed as vigorous.

(C) *Foliage.*—Long narrow variegated foliage, opposite on vegetative stems, in whorls of 5–8 leaves in flowering state. (1) Size: 10–11 cm. long by 2–3 wide (flattened); highly concaved under strong light to reflexing at maturity. (2) Shape: Lanceolate, apex acuminate slightly twisted, base acute. (3) Texture: Upper surface rugose, reverse glabrous. (4) Margin: Nearly entire to slightly finely serrated. (5) Color: Young foliage, top side yellow green 147-A; under side yellow green 147-B; mature foliage top side green 139-A; under side yellow green 146-A. Basal and mid-rib variegation yellow 16B. (6) Venation: Pinnate.

Flowering description:

(A) *Flowering habits.*—Leaf whorl usually contains 7–8 flower buds opening progressively as whorl develops, with last flowers still blooming as flowers in next whorl begin to open. Records show that individual flowers have remained in good condition for up to 20 days which would be considered unusually long for hybrid New Guinea Impatiens.

(B) *Natural flowering season.*—Indeterminate, with continuous flowering year around; flower quantity and time for opening directly related to light.

(C) *Flower buds.*—Ellipsoidal with 5 cm. long open throated dark red spur originating from the major sepal; flowers perfect.

(D) *Flowers borne.*—On rather short pedicels, keeping flowers close to foliage thus accentuating flower color and foliage contrast; dark pink to red throat in flower gives further flower accent.

(E) *Quantity of flowers.*—Average 6–8 flowers per whorl of leaves.

(F) *Petals.*—(1) Shape: Heart-shaped, top very dominant, central pair smallest. (2) Color, top side in summer when opening, red 55-B, fading to red 55B-C; under side 55B-C. (3) Number of petals: Five (5). (4) Size of flowers: 6–7 cm. in diameter.

(G) *Reproductive organs.*—(1) Stamens: Five (5) in number. (a) Anther shape: Hooded, color red purple 66-B. (b) Pollen color: Cream. (2) Pistils (a) Stigma: Five (5) in number; segmented column-shaped, color green tint. (b) Style: Colorless. (c) Ovaries: Five (5) in number, celled; size 4.5–5 mm. long before fertilized, green in color.

*Capsule.*—Explosively dehiscent.

Disease resistance: No known major disease or insect problems observed to date other than botrytis petal rot under very adverse weather conditions.

I claim:

1. A new and distinct cultivar of impatiens known by the cultivar name Gemini, as disclosed and illustrated, and particularly characterized by its clear bright pink flower color and contrasting dark green variegated foliage; highly floriferous habit; firm petal texture, relatively large flowers, with distinct deep pink to red throat; continuous flowering and highly stable flower color, with little fading in summer, and by its semi-procumbent and weather resistant habits which make it ideal for baskets and bedding plants.

* * * * *

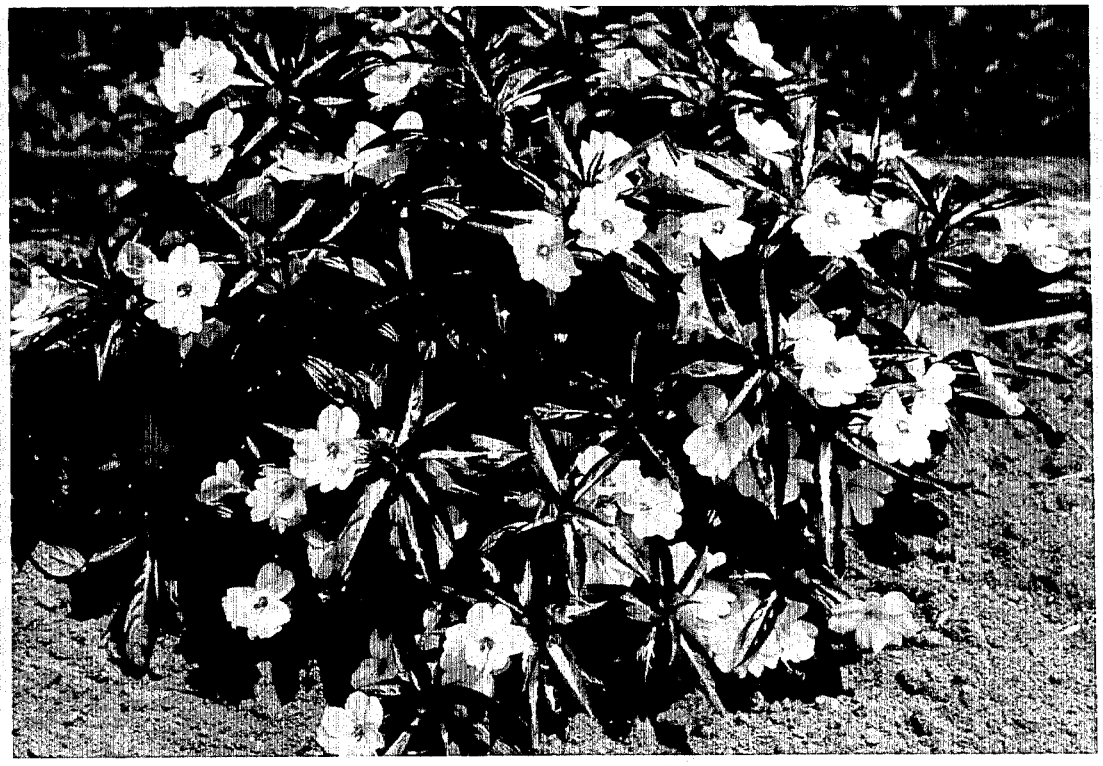

UNITED STATES PATENT AND TRADEMARK OFFICE

CERTIFICATE OF CORRECTION

PATENT NO. : PP5132

DATED : November 1, 1983

INVENTOR(S) : JAMES C. MIKKELSEN

It is certified that error appears in the above—identified patent and that said Letters Patent is hereby corrected as shown below:

The color photographic drawing appearing with this plant patent should be the color photographic drawing as shown per attached.

Signed and Sealed this

*Eleventh* Day of *September 1984*

[SEAL]

*Attest:*

GERALD J. MOSSINGHOFF

*Attesting Officer*

*Commissioner of Patents and Trademarks*